US009533323B2

(12) United States Patent
Sauzade

(10) Patent No.: US 9,533,323 B2
(45) Date of Patent: Jan. 3, 2017

(54) ULTRASOUND LIQUID ATOMIZER

(75) Inventor: Jean-Denis Sauzade, Grasse (FR)

(73) Assignee: TELEMAQ, Mouans-Sartoux (FR)

( * ) Notice: Subject to any disclaimer, the term of this patent is extended or adjusted under 35 U.S.C. 154(b) by 1096 days.

(21) Appl. No.: 12/514,345

(22) PCT Filed: Nov. 12, 2007

(86) PCT No.: PCT/EP2007/062234
§ 371 (c)(1),
(2), (4) Date: Jun. 16, 2009

(87) PCT Pub. No.: WO2008/058941
PCT Pub. Date: May 22, 2008

(65) Prior Publication Data
US 2010/0044460 A1    Feb. 25, 2010

(30) Foreign Application Priority Data
Nov. 14, 2006  (FR) .................... 06 09905

(51) Int. Cl.
*B05B 1/08*    (2006.01)
*B05B 17/00*   (2006.01)
(Continued)

(52) U.S. Cl.
CPC ......... *B05B 17/0646* (2013.01); *A61M 11/005* (2013.01); *A61M 15/0085* (2013.01); *B05B 17/063* (2013.01)

(58) Field of Classification Search
CPC ............. B05B 17/0646; B05B 17/0607; B05B 17/0638; B05B 17/063; B05B 17/0623
(Continued)

(56) References Cited

U.S. PATENT DOCUMENTS 2,855,244 A * 10/1958 Camp ................... 239/102.2
2,949,900 A *  8/1960 Bodine .................. B01J 19/10
                                                            123/198 E
(Continued)

FOREIGN PATENT DOCUMENTS

EP     0 432 992     6/1991
EP     1 386 672     2/2004
(Continued)

OTHER PUBLICATIONS

International Search Report for PCT/EP2007/062234, mailed Apr. 10, 2008.
(Continued)

*Primary Examiner* — Jason Boeckmann
(74) *Attorney, Agent, or Firm* — Nixon & Vanderhye P.C.

(57) ABSTRACT

The invention relates to an ultrasound liquid atomizer comprising: a rigid piezoelectric transducer body (1) having a first end defining an opening and a second end, the inside of the piezoelectric transducer body (1) comprising a cavity for containing a liquid to be atomized and said body (1) further comprising a symmetry axis; a micro-perforated membrane (3) attached on said first end and covering said opening; a piezoelectric member (2, 9) adapted and provided so as to vibrate the piezoelectric transducer body (1); characterized in that the piezoelectric member (2, 9) is located towards said second end in order to vibrate the piezoelectric transducer body (1) in a direction parallel to its symmetry axis.

36 Claims, 9 Drawing Sheets

(51) Int. Cl.
*A61M 11/00* (2006.01)
*A61M 15/00* (2006.01)
*B05B 17/06* (2006.01)

(58) Field of Classification Search
USPC ......... 239/102.1, 102.2, 370, 337, 340, 343;
5/102.1, 102.2, 370, 337, 340, 343
See application file for complete search history.

(56) References Cited

U.S. PATENT DOCUMENTS

| | | | |
|---|---|---|---|
| 3,103,310 A | | 9/1963 | Lang |
| 4,153,201 A | | 5/1979 | Berger et al. |
| 4,300,546 A | * | 11/1981 | Kruber ................... 128/200.16 |
| 4,326,275 A | * | 4/1982 | Butler ........................... 367/160 |
| 4,337,896 A | * | 7/1982 | Berger ............... B05B 17/0623 239/102.2 |
| 4,479,609 A | | 10/1984 | Maeda et al. |
| 4,496,101 A | * | 1/1985 | Northman ................. 239/102.2 |
| 4,533,082 A | | 8/1985 | Maehara et al. |
| 4,541,564 A | * | 9/1985 | Berger et al. ............. 239/102.2 |
| 4,585,167 A | | 4/1986 | Kholin |
| 4,655,393 A | | 4/1987 | Berger |
| 4,723,708 A | * | 2/1988 | Berger et al. ............. 239/102.2 |
| 4,850,534 A | * | 7/1989 | Takahashi et al. ........ 239/102.2 |
| 4,978,067 A | * | 12/1990 | Berger et al. ............. 239/102.2 |
| 5,134,993 A | | 8/1992 | Van der Linden et al. |
| 5,170,782 A | | 12/1992 | Kocinski |
| 6,357,671 B1 | * | 3/2002 | Cewers ...................... 239/102.2 |
| 6,394,363 B1 | * | 5/2002 | Arnott et al. ............. 239/102.1 |
| 6,640,804 B2 | * | 11/2003 | Ivri et al. ................. 128/200.16 |
| 6,651,650 B1 | * | 11/2003 | Yamamoto et al. ..... 128/200.16 |
| 7,883,031 B2 | * | 2/2011 | Collins et al. ............ 239/102.2 |
| 2002/0129812 A1 | | 9/2002 | Litherland et al. |
| 2002/0162898 A1 | * | 11/2002 | Klimowicz et al. ....... 239/102.1 |
| 2005/0034719 A1 | | 2/2005 | Feiner et al. |
| 2005/0056274 A1 | | 3/2005 | Kunschir |
| 2005/0224076 A1 | | 10/2005 | Pfichner et al. |
| 2006/0102172 A1 | | 5/2006 | Feiner et al. |
| 2006/0243277 A1 | | 11/2006 | Denyer et al. |

FOREIGN PATENT DOCUMENTS

| | | |
|---|---|---|
| JP | 58-067374 | 4/1983 |
| JP | 58-67374 | 4/1983 |
| JP | 61-141955 | 6/1986 |
| JP | 5-277188 | 10/1993 |
| JP | A 5-277188 | 10/1993 |
| JP | 2003-265994 | 9/2003 |
| JP | A 2005-537870 | 12/2005 |
| JP | A 2006-506150 A | 2/2006 |
| JP | A 2006506150 A5 | 4/2006 |
| WO | 93/10910 | 6/1993 |
| WO | WO 2004/022132 A2 | 3/2004 |

OTHER PUBLICATIONS

English Translation of International Search Report for PCT/EP2007/062234, mailed Apr. 10, 2008.

Japanese Office Action dated May 8, 2012 for applicant's Japanese Patent Application No. 2009-536715 corresponding to PCT/EP2007/062234 filed Nov. 12, 2007, and its English translation.

Japanese Office Action dated Jan. 28, 2014, for applicant's Japanese Patent Application No. 2009-536715 corresponding to PCT/EP2007/062234 filed Nov. 12, 2007, and its English translation.

Berger, Harvey L., "Coating Drug-Eluting Arterial Stents Using Ultrasonic Spray Nozzles," ILASS Americas, 19th Annual Conference on Liquid Atomization and Spray Systems, Toronto, Canada, May 2006, 6 pp.

Japanese Office Action mailed Jun. 3, 2014 issued in Japanese Patent Application No. 2013-185297, 3 pp.

Japanese Office Action mailed Jun. 10, 2014 issued in Japanese Patent Application No. 2013-17255, 3 pp.

Maehara, Naoyoshi et al., "Influence of the Vibrating System of a Multipinhole-Plate Ultrasonic ebulizer on its Performance," Rev. Sci. Instrum. 57 (11), Nov. 1986, pp. 2870-2876.

Maehara, N. et al., "A Pinhole-Plate Ultrasonic Atomizer," Ultrasonics, Nov. 1984, pp. 259-260.

Peskin, Richard L. et al., "Ultrasonic Atomization of Liquids," The Journal of the Acoustical Society of America, vol. 35, No. 9, Sep. 1963, pp. 1378-1381.

* cited by examiner

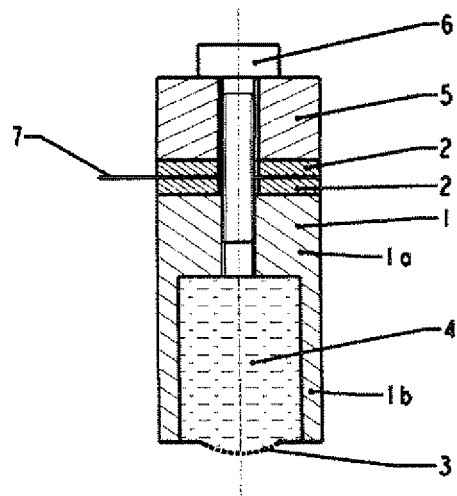
Fig. 1.A
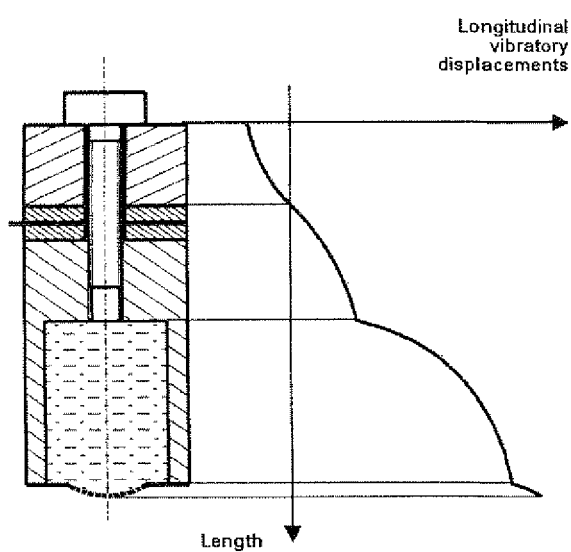
Fig. 1.B
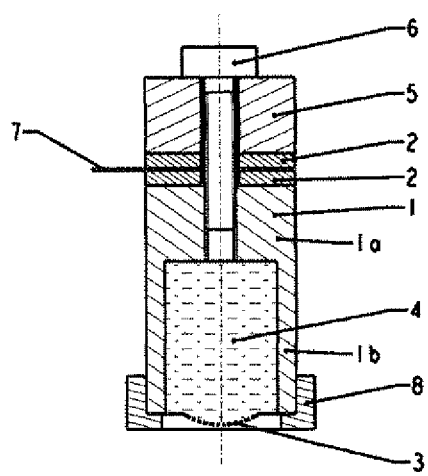
Fig. 2

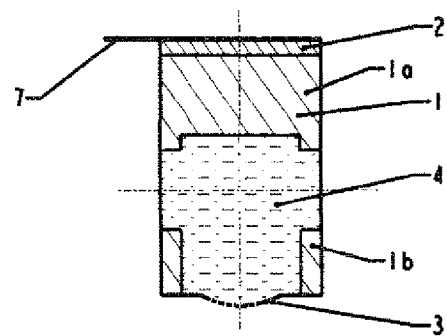
Fig. 6
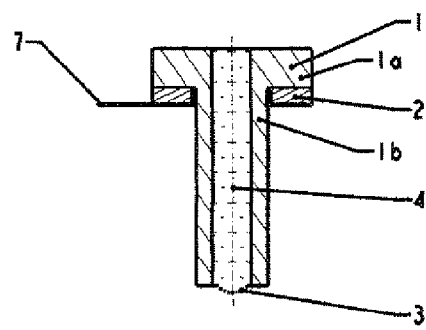
Fig. 7
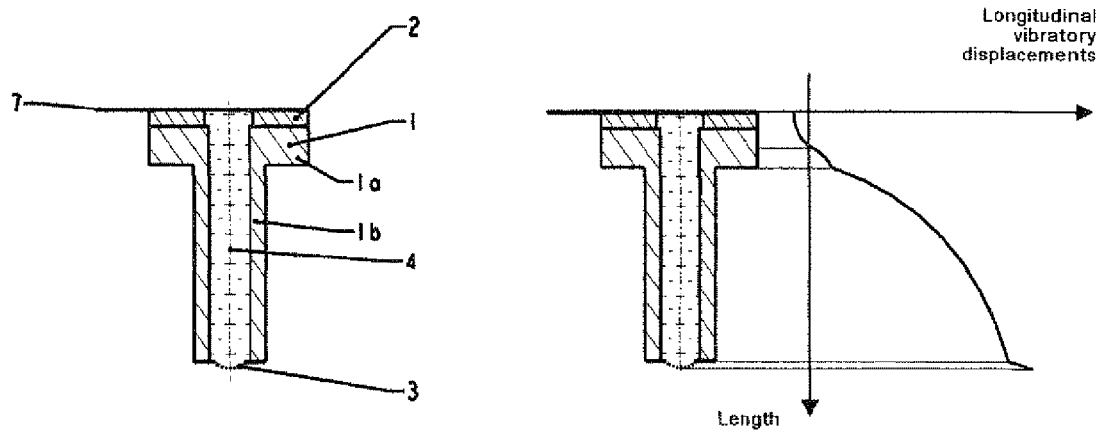
Fig. 8.A      Fig. 8.B

| Fig 11.A | Fig 11.B | Fig 11.C | Fig 11.D |
| Mode 1 : Flexing | Mode 1 : Flexing | Mode 2 : Flexing | Piston mode |

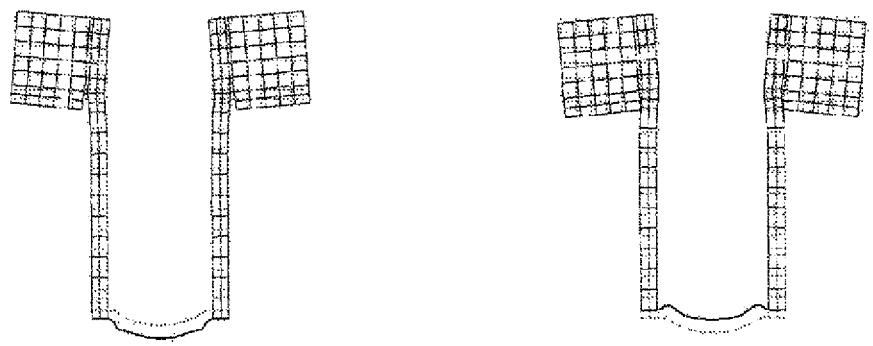
Fig 12.A : 77 kHz mode
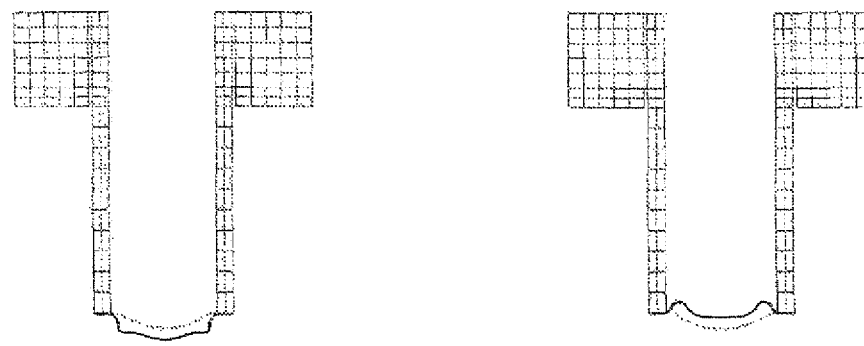
Fig 12.B : 120 kHz mode
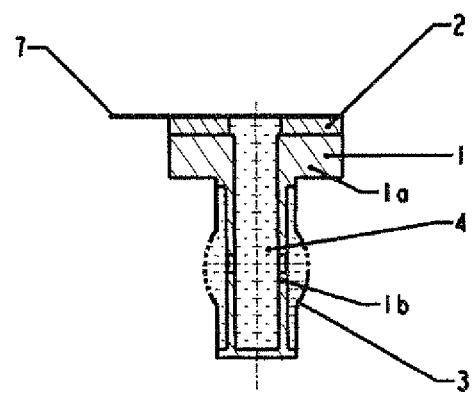
Fig. 13

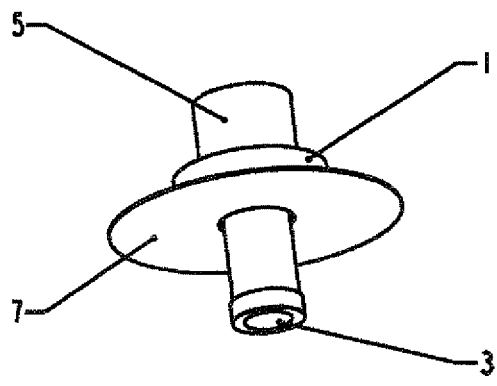
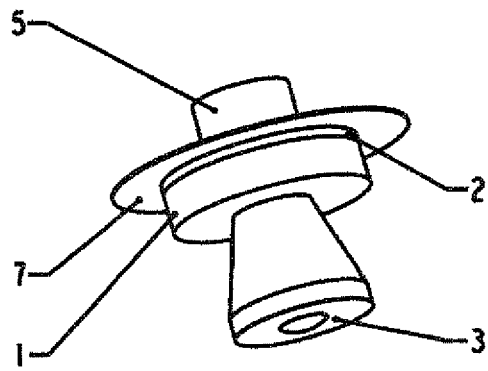
Fig. 14.A          Fig. 15.A
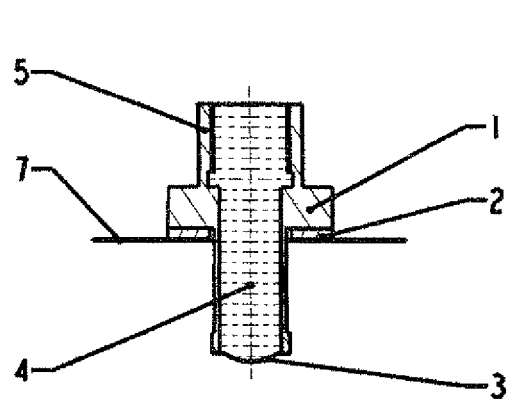
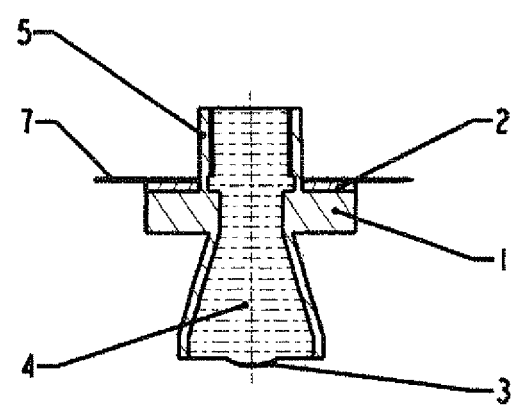
Fig. 14.B          Fig. 15.B

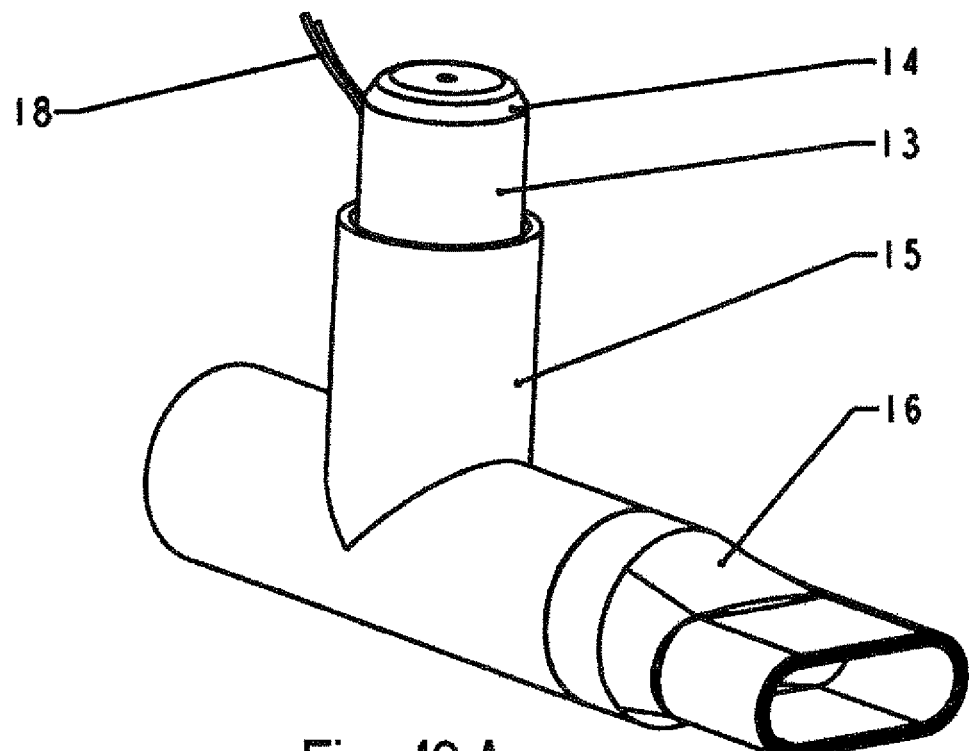
Fig. 16.A
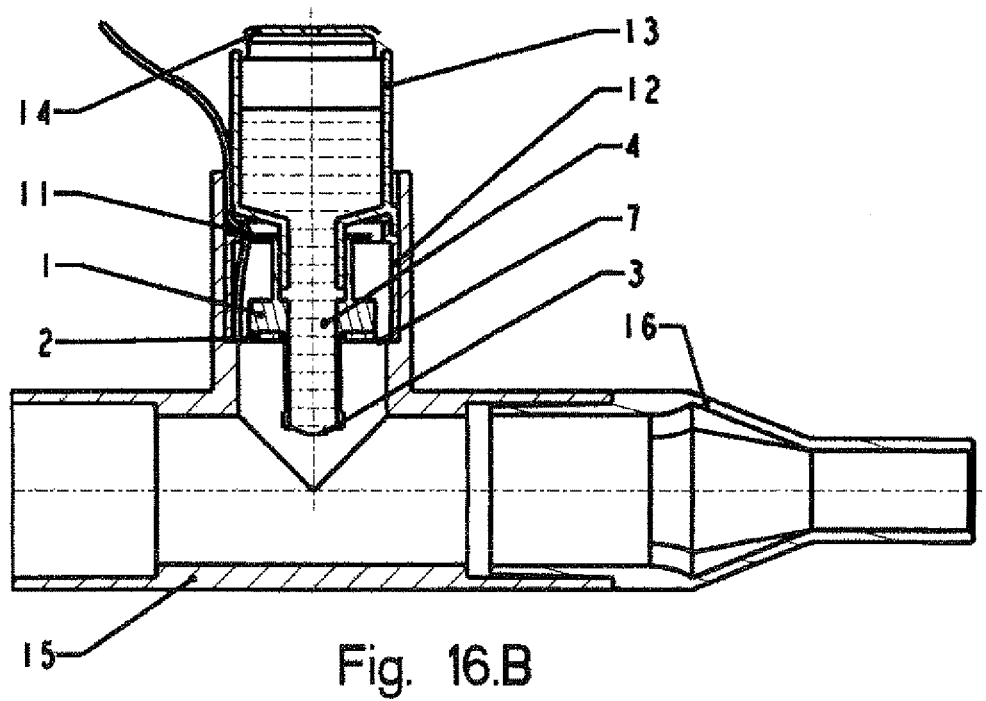
Fig. 16.B

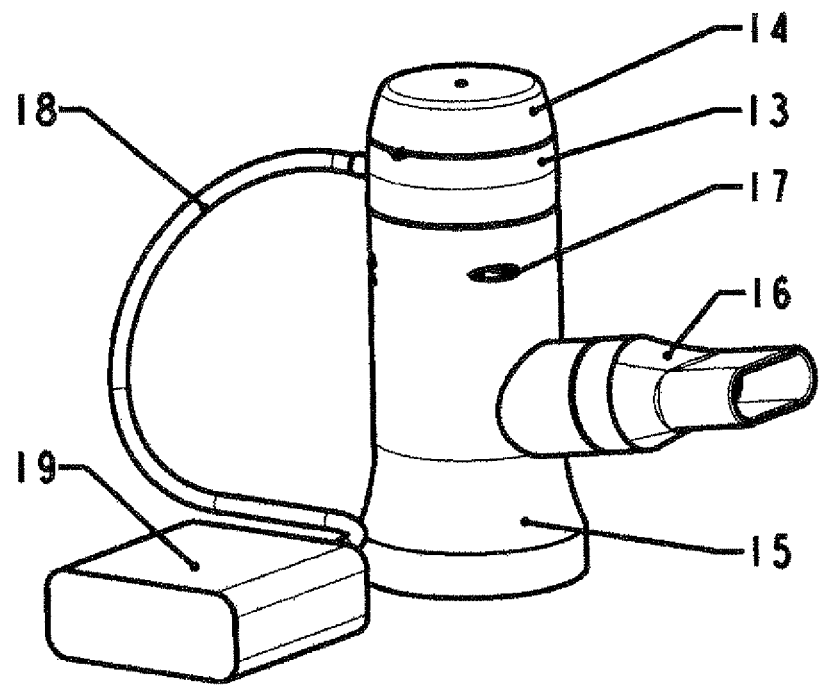
Fig. 17.A
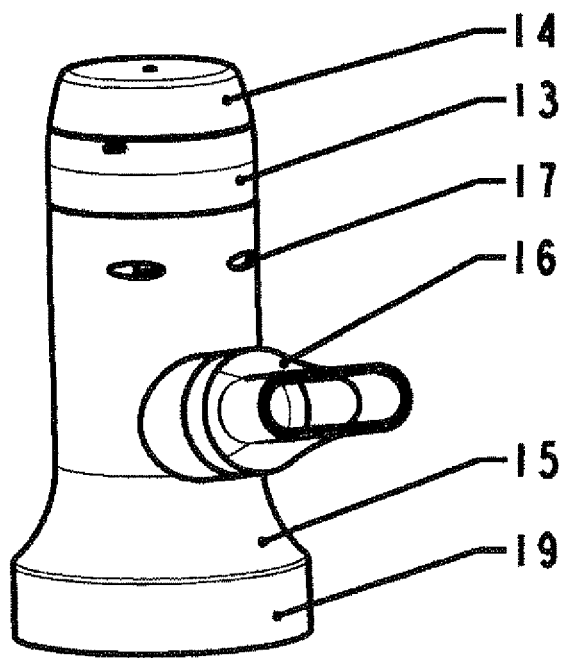
Fig. 17.B

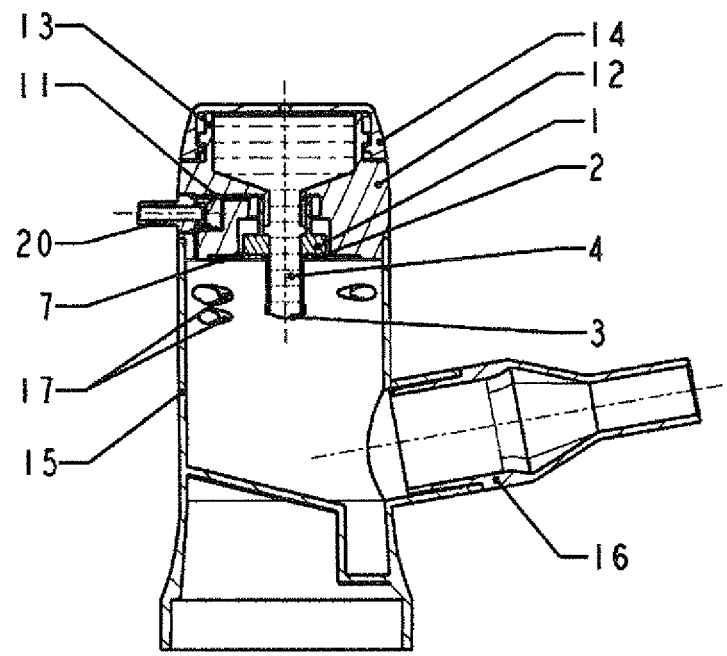
Fig. 17.C
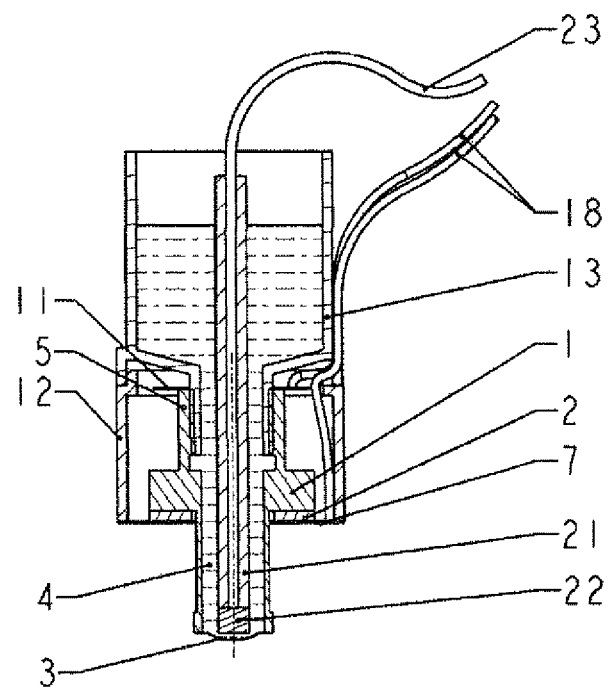
Fig. 18

ULTRASOUND LIQUID ATOMIZER

This application is the U.S. national phase of International Application No. PCT/EP2007/062234, filed 12 Nov. 2007, which designated the U.S. and claims priority to French Application No. 06 09905, filed 14 Nov. 2006, the entire contents of each of which are hereby incorporated by reference.

FIELD OF THE INVENTION

The present invention relates to fluid dispensers, commonly called atomizers, that are used to accurately diffuse, by means of piezoelectric members, fluids in the form of micro-droplets or aerosols.

STATE OF THE ART

In many applications, fluids or liquids, whatever their nature (oily, aqueous or alcoholic), whether they are solutions or suspensions (particles suspended in a liquid), are dispensed by micronization, atomization, vaporization or aerosol generation. The main applications that use these fluid dispensing devices relate to the administration of medicines (pharmacy), the diffusion of cosmetic products (in particular perfumes), disinfection, odor generation, humidification of air or media (paper, fabrics, etc.) and the dispensing of biological reagents.

Regarding medical applications, nebulizers have been employed for decades to deliver medicines by inhalation. The devices used for tins purpose can include a mechanical dosing pump, a pneumatic or ultrasound nebulizer. Until recently, these devices were designed to deliver medicines through respiratory pathways, at a relatively superficial level. For some years, the pharmaceutical industry has been addressing the administration of medicines in the form of aerosols as deep as possible into the lungs in order to reach the bronchioles. By being able to do this, it would be possible to administer systemic medicines or genes by respiratory pathway.

For this, it is necessary to develop new technologies to enhance the efficiency, the accuracy and the uniformity of the aerosols intended to be deposited in the bronchioles. The conventional devices are generally limited either by an excessively fast expulsion of the aerosol, or by excessive consumption, or by degradation of the medicinal products, or by excessively large droplets, or by noise.

To satisfy the new conditions demanded by the delivery of medicines by respiratory pathway, a number of manufacturers of aerosol generators have developed devices based on vibrating micro-perforated grids or membranes. These manufacturers include Nektar (Aeroneb), Odem (Touch-Spray), Pari (e-Flow), Pfeiffer (MicroHaler), Omron (NE-UO22), Sheffield Pharmaceutical (Premaire), Alexza (Staccato).

The first studies concerning ultrasound atomizers including a vibrating micro-perforated membrane were carried out by the Matsushita research laboratory in the 1980s. The principle of the ejection of liquid in fine droplets through a micro-perforated vibrating membrane subject to vibration is developed in particular in the following publications: Ueha S., et al. Mechanism of ultrasonic atomisation using a multi-pinhole plate. Acoust. Soc. Jpn. (E) 6, 1:21 (1985). Maehara N., et al. Influence of the vibrating system of a multipinhole-plate ultrasonic nebutizer on its performance. Review of scientific instruments, 57 (11), November 1986, pp. 2870-2876. Maehara N., et al. A pinhole-plate ultrasonic atomizer. Ultrasonics November 1984.

All of these studies have formed the subject of a number of patents, in particular U.S. Pat. No. 4,533,082 (1985) and U.S. Pat. No. 4,605,167 (1986) which describe an atomizer that uses a vibrating membrane perforated with micro-holes. The membrane includes a curved part protuberance or dome) at its center causing the droplets generated to diverge. The membrane includes micro-perforations of 30 to 100 μm diameter. The vibrating member is an annular piezoelectric ceramic with an external diameter of 5 to 15 mm, an internal diameter of 2 to 8 mm. The vibrating membrane that is 30 to 120 μm thick is glued to the annular ceramic. This piezoelectric ceramic is excited at frequencies between 30 and 200 kHz on its radial deformation mode. Bespack U.S. Pat. No. 5,152,456 (1992), see also the corresponding European application, EP 0 432 992 A1, takes up the principle proposed by Matsushita. However, the vibrating member (or vibrator) comprises an annular disk of aluminum that is 22 mm in diameter. The piezoelectric ceramic is fixed to this aluminum disk. The operating mode of the piezoelectric ceramic corresponds to a radial deformation. The central opening of the aluminum disk is 4 mm. The nickel membrane has 1500 perforations (or holes) of 3 μm diameter.

The Toda U.S. Pat. No. 5,297,734 (1994) refers to a vibrating-plate-type atomizer of square geometry allowing throughputs up to 1 l/hour. The atomizer comprises a nickel membrane 50 μm thick glued to a piezoelectric ceramic disk with an external diameter of 24 mm, an internal diameter of 12 mm and a thickness of 6 mm. The membrane has tapered holes with an internal diameter of 1 mm and external diameter of 20 μm.

The Technology Transfer Partnership (TTP) U.S. Pat. No. 5,261,601 (1993) describes an atomizer based on the above-mentioned Bespack patent. The TTP U.S. Pat. No. 5,518,179 (1996) refers to a disk atomizer in which the perforated membrane is made of electroformed nickel. The TTP atomizer requires no liquid chamber behind the membrane and the liquid is fed by capillarity (use of wick or porous material). The TTP atomizer highlights its bimorphic structure specifying the flexing mode of the assembly consisting of the piezoelectric ceramic and the micro-perforated membrane. The membrane has a rigidity comparable to that of the annular piezoelectric ceramic. The reference atomizer comprises a brass ring with an external diameter of 20 mm and a thickness of 200 μm. The piezoelectric ceramic ring has an external diameter of 20 mm, an internal diameter of 6 mm and a thickness of 200 μm. The Aerogen U.S. Pat. No. 6,085,740 (2000) mentions a means for atomizing a liquid in fine droplets by using a micro-grid. The membrane, provided with micro-holes of 1 to 6 μm diameter, is vibrated by a piezoelectric bimetallic strip operating at 45 kHz. The liquid is fed by capillarity and the membrane can be dissociated from the vibrator.

The Aerogen U.S. Pat. No. 6,427,682 (2002) describes the use of a medicine diffusing appliance that uses a vibrating membrane. Its principle is very close to that of Matsushita. It comprises a part made of aluminum vibrated by flexing using an annular piezoelectric ceramic. The vibrating membrane provided with micro-holes is produced by electroforming. A chamber containing the liquid is in contact with the membrane.

Moreover, Omron has developed an ultrasound pump technology making it possible to atomize a liquid through a micro-perforated membrane. This technology is described in U.S. Pat. No. 6,901,926 (2005). In the Omron technology, the micro-perforated membrane is not vibrated directly by the vibrating member. The droplets are formed by ejection of the liquid through the holes when the pressure varies dynamically due to the ultrasound pump.

The piezoelectric or ultrasound atomizers of the state of the art (frequency greater than 20 µm) that include a micro-perforated membrane that is subjected to vibration all operate by flexing of the membrane and the piezoelectric ceramic associated therewith. In fact, it involves combining in different ways an annular piezoelectric ceramic and a thin metallic membrane that includes a large number of micro-perforations. This type of structure benefits from a small thickness.

The devices of the state of the art do, however, have a number of drawbacks.

A first drawback lies in the fact that the micro-perforated membrane contributes strongly to the resonance mode of the atomizer. The effect of this phenomenon is that the atomizer is itself greatly damped in its resonance by the liquid that is in contact with the membrane. The operation of the atomizer depends strongly on the quantity of liquid or the pressure exerted by the liquid behind the membrane. This creates a complication in the control of the atomizer's excitation frequency. Furthermore, this damping leads to an overheating of the vibrating member and of the membrane. This overheating causes the operating time of the atomizer to be limited, the electrical consumption required for the latter to operate to be increased and can lead to a degradation of the properties of the liquid to be atomized. Moreover, in this type of structure, the deformation of the membrane by flexing does not make it possible to obtain a uniform displacement over the entire surface of the membrane. Depending on the positioning of the micro-holes on the membrane, the latter do not have the same throughput and the aerosol generation can be unstable (threshold effect). Also, the sensitivity of the vibrating structure to the mechanical fixings and the liquid seals (spurious damping) make the technological solutions for industrially implementing such structures in large quantities and at low cost both complex and costly.

There is therefore a need to remedy these various drawbacks and propose devices that are more robust, easier to control electronically, more energy-efficient, easier to industrialize in large quantities and at low cost.

GENERAL DESCRIPTION OF THE INVENTION

The present invention sets out to remedy in particular the problems explained in the preceding section.

To this end, its subject is an atomizer as defined in the main claim.

Preferred embodiments are the subject of the dependent claims.

In the present text, the term "transducer" should be understood to mean a member comprising a piezoelectric transducer body, at least one piezoelectric member and, optionally, a rear mass.

The term "section" should be understood to mean a geometrical figure comprising the intersection of a plane and a volume. Thus, considering the example of a cylindrical object with a variable internal diameter, it will be said that it has a section that varies over its length.

The transducer body has a symmetry axis.

A number of the advantages offered by the atomizer according to the present invention result from the fact that the piezoelectric transducer body to which the membrane is fixed vibrates in a longitudinal mode, that is, in a direction parallel to the symmetry axis of the piezoelectric transducer body.

One or more piezoelectric members can be provided.

Preferably, the section of the piezoelectric transducer body varies over its length.

According to one embodiment, the section varies discontinuously.

Advantageously, the section varies abruptly at a single point.

Such a section variation is illustrated in the following embodiment in which the piezoelectric transducer body has two parts with different external diameters. The deformation amplification zone, the end of which includes the membrane, has the smallest diameter. In this configuration, called "horn" in this text, the longitudinal ultrasound waves are amplified in displacement at the change of section of the transducer. The tubular member acts as a micronic longitudinal displacement amplifier.

According to another embodiment of the invention, the membrane at least partially forms a dome that provides a number of functions. Commonly in the prior art, the micro-perforated membrane is designed to retain the liquid in the atomizing chamber behind the membrane and contain its static pressure. The balance of the pressures, the shape of the holes and the nature of the material used for the membrane is such that the liquid does not seep out of the membrane and that no "dripping" or liquid loss phenomenon occurs. Moreover, the dome shape provides for a better distribution of the micro-droplet or aerosol mist by causing the jet to diverge by simple geometrical effect. Also, the vibratory speed associated with the displacement of the membrane makes it possible to eject the micro-droplets through the holes. In the case of the present invention, the dimensions of the dome and of the micro-perforated membrane are such that the dome provides a vibratory motion amplification effect while retaining a vibratory speed distribution that is uniform over the surface of the membrane. Unlike in the prior art, the membrane does not affect the vibratory behavior of the transducer. Whatever the thickness of the membrane (for example from 20 to 200 µm), the piezoelectric member retains its dynamic characteristics and its vibratory performance. More specifically, the resonance frequency and the vibratory displacements of the transducer are not modified by the mechanical coupling of the membrane. This gives the atomizer advantages in as much as the transducer (frequencies, vibratory displacements, deformation modes, coupling coefficient and mechanical quality factor) can be designed without taking into account the membrane (geometry and material).

This property of the present invention advantageously makes it possible to optimize the structure of the transducer (or converter) in order to favor either the aerosol output speed, or the throughput, or the resonance frequency, or the consumption or the efficiency of the transducer. In this way, it is possible to produce vibrating membrane atomizers that allow aerosols to be produced at almost zero speed (medical application) up to ejection speeds for example of the order of 30 m/s (cosmetic application). Similarly, the atomization throughput is no longer directly linked to the surface area of the piezoelectric ceramic but to the length of the piezoelectric transducer making it possible to adapt throughputs from 1 µl/s to 300 µl/s. It is this same length that directly governs the resonance frequency of the atomizer. The atomizer operating mode is not a flexing mode but a longitudinal elongation mode. This makes it possible to work at high frequencies (50 to 200 kHz) with piezoelectric ceramics of small diameter without compromising the liquid throughput and above all with very low losses. These mechanical losses which correspond to an energy that is dissipated in heat in the transducer increase strongly according to the operating frequency of the transducer. In the present invention, the latter are reduced because the efficiencies of the longitudinal-transducer-type structures are far better than the "bimetallic strip" type structures that operate by flexing.

The low losses in the transducer lead to the design of atomizers with low electrical consumption. This advantage is considerable in as much as the atomizers of the prior art are limited in their application by the atomization time and the lifetime of the power supply cells or batteries. In practice, the advantageous applications of the vibrating micro-perforated membrane atomizers mainly relate to "hand-held" devices operating on cells or batteries. The structure that is the subject of the present invention is less damped by the liquid behind the membrane. This property provides for less heating of the liquid to be atomized. In the applications in which the atomizers deliver medical formulations, heating of the liquid can be prohibitive and greatly limit the benefit of such atomizers.

Moreover, according to a preferred embodiment the present invention is characterized by the fact that the vibration nodes can be accessed to enable the atomizer to be mechanically fixed easily. The atomizers of the prior art that operate by flexing of the annular ceramic are difficult to fix mechanically without disturbing and greatly damping the vibration mode. In the case of the present invention, the atomizer is preferably mechanically fixed or overmolded in the area of the vibration node (this node is unique) and allows for very simple and very inexpensive mechanical assembly and sealing solutions.

Another characteristic of the invention is that the liquid can be placed directly in contact with the rear face of the membrane. In practice, the vibration mode of the atomizer in a longitudinal mode has little sensitivity to the presence of a liquid and to the weight of the column of this liquid.

This property enables the atomizer to operate equally at any angle from the vertical to the horizontal. The liquid can also be guided to the membrane by capillarity by using ducts, wicks or appropriate porous materials. In this way, the liquid reservoir can be located above, around or below the atomizer. According to a variant of the invention, the structure of the atomizer comprises a rear mass, also called dynamic mass, the role of which is to prevent the transducer from vibrating backward, two piezoelectric ceramics linked by common connections, a vibratory movement amplifier including a cavity and a micro-perforated membrane of varied shape but preferably dished forming a protuberance or dome.

According to another variant of the invention, a prestressing mechanism like a screw can be used to mechanically link the rear mass, the ceramics and the amplifier. The amplifier is metallic and preferably made of stainless steel, titanium or aluminum. The micro-perforated membrane is glued to the vibratory amplifier. The membrane, which has little effect on the vibratory behavior of the atomizer, can be made of a variety of materials such as plastic, silicon, ceramic, but is preferably made of metal. The micro-perforations can be produced by different means but preferably by electroforming or by laser. The quantity of micro-perforations can range from one hole for the dispensing of liquid on demand, to several thousands of holes. The size of the micro-holes or the mesh of the grids can range from 1 μm to 100 μm in equivalent diameter according to the applications of the atomizer. It has been demonstrated that the throughput and uniformity performance of the jet of droplets from the atomizer were greatly dependent on the displacement mode of the membrane. These performance levels are enhanced if the membrane is displaced in "piston" mode without deformation by flexing. In the state of the art, the atomizers operate by flexing and therefore lead to one or more vibration nodes inside the membrane. In the present invention, the membrane is not involved in the vibration mode of the transducer and it is possible to engineer and optimize the geometry of the membrane in order for the latter to be deformed in "piston" mode. For this, modelings and test results show that the diameter of the protuberance (or dome) must be close to the diameter of the cavity containing the liquid (or chamber). This means that the maximum height of the dome must be close to half the internal diameter of the cavity.

The displacement of the membrane in "piston" mode means that the vibratory speed on the surface of the membrane can be made uniform. The result of this is that the micro-perforations (or holes) eject micro-droplets of sizes that are better calibrated and with an identical throughput when they are compared with each other.

Other embodiments of the invention are briefly described below:

- The piezoelectric member or members is/are represented by a single ceramic fixed with a glue of sufficient rigidity to the transducer subject to the vibratory movement.
- The piezoelectric ceramic is a multilayer allowing for a low-voltage electrical power supply (1 to 15 $V_{DC}$) such as can be supplied, for example, by the companies Epcos, Fuji, Noliac, Morgan Matroc or Physic Instruments.
- The piezoelectric ceramic is fixed to the body of the transducer so that there is no contact between the latter and the liquid to be atomized. This configuration makes it possible to electrically insulate the piezoelectric ceramic and eliminate any problem of seal-tightness and of compatibility (medical application) with the liquid.
- The vibratory displacement amplifier (or "horn") of the atomizer includes passages, grooves or holes so that the chamber or reservoir of liquid is located around the horn.
- The piezoelectric transducer of the atomizer includes a "bell mouth" at the end of the "horn" which preferably vibrates according to a "piston" mode without any flexing. This "bell mouth" has the advantage of amplifying the vibratory displacement of the transducer but also of being able to fix a micro-perforated membrane of larger diameter. This configuration is for increasing the throughput of the atomizer despite its small size.
- The piezoelectric transducer, operating in longitudinal mode, causes a micro-perforated membrane or a cylindrical grid to vibrate and be deformed. To optimize the displacement of the cylindrical membrane that is placed between the transducer and the bell mouth, a protuberance can be added in order to increase the rigidity of the membrane appropriately.
- The atomizer includes a "horn" of particular shape such as, for example, a truncated cone allowing for an amplification of vibratory movement by abrupt change of section. In this particular configuration, the ratio of the membrane-piezoelectric member distance to the diameter of the piezoelectric member is preferably greater than 0.5.

The micro-perforated membrane or grid is not glued but acoustically coupled to the transducer by mechanical pressure means.

The fixing of the atomizer to an external medium is provided by a foil or a flexible circuit fixed by mechanical means or by gluing to the electrode of the ceramic that is not associated with the transducer. This particular fixing method is advantageous due to its simplicity of implementation and its low cost. This configuration has the advantage of decoupling the transducer from the external medium (static resistance) and of not disturbing its dynamic operation. Moreover, the metal foil (or the flexible circuit) makes it possible to supply the piezoelectric ceramic with electricity.

The atomizer comprises a transducer body which includes a means of fixing a reservoir without disturbing its dynamic operation and without affecting its performance.

The atomizer includes a reservoir that is mechanically fixed to the body of the transducer without disturbing the operation of the latter.

The atomizer includes a solid or hollow mechanical unit made of different materials but preferably plastic, placed coaxially inside the cavity containing the liquid, of varied shape but preferably cylindrical, the role of which is to guide the air bubbles that could be formed at the level of the vibrating membrane and that would block the atomization process.

The atomizer includes a liquid presence sensor comprising an electrode placed inside the "horn" and close to the vibrating membrane. A low-frequency alternating electrical current is applied to this electrode, the signal of which is recovered on the electrical ground of the transducer by processing. The alternating current is propagated from the electrode to the vibrating membrane via the conductivity of the liquid. The presence or the absence of this signal indicates the presence or the absence of liquid.

The atomizer is placed in a housing of varied shape that can be held in the hand or applied to a part of the body (human or animal) such as a mask, and made of different materials but preferably plastic. This housing can constitute a diffuser of perfume, of moisture, of disinfectant or of medicine. More particularly, the atomizer associated with the housing can be used as a device for delivering medicine by pulmonary, nasal or ocular pathway.

The atomizer can be associated with a housing dedicated specifically to the delivery of medicine by pulmonary pathway. This housing can include all of the functions that make it possible to manage the inhalation or the diffusion of this medicine. In particular, it will include a tip or anatomic adapter which may be disposable, an assembly of valves or of chicanes making it possible to better manage the flow of air (sucked or blown), a device for triggering atomization on inhalation which can be produced either mechanically or electronically, a reservoir either at ambient pressure or with a depressurized (sterile) controlled atmosphere, a liquid level sensor and a mechanism to avoid the formation of air bubbles as described in this patent. In this text, this assembly is designated "inhaler".

The atomizer, incorporated in a mechanical housing, can be electronically controlled by an external electronic module making it possible to supply it with power by cell, batteries or mains. This same electronic module can be incorporated in the mechanical module in order to ensure complete autonomy of the device. This incorporated electronic module can be powered by a battery, a cell or a rechargeable super-capacitor or by the mains or by induction effect.

The atomizer includes an electronic scale-removing, or more generally declogging, function produced by a particular electrical power supply mode by applying electrical voltage cycles to the piezoelectric members of duration, amplitude or frequency that are different from the nominal electronic power supply. This declogging mode can be implemented while the atomizer is dipped in a bath of scale-removing, cleaning or sterilizing product.

The atomizer includes a membrane with holes of micronic size, the diameter of which has been reduced by means of a surface treatment (polymer or metallic), more particularly by electrolytic gold deposition. Moreover, these different surface treatments help to reduce the dripping or clogging phenomena and in certain cases provide bactericidal, virucidal or biocompatibility functions.

The atomizer is made of materials or includes a surface treatment making it possible to ensure its cold or hot sterilization (stoving). In particular, the atomizer will include high temperature piezoelectric ceramics (>150° C.), a stainless steel or titanium transducer, a membrane covered with an electrolytic gold flash.

The atomizer is electrically connected so that the electrical potential of the membrane is different from the electrical ground of the electronic module. This electrical configuration makes it possible to electrically charge the micro-droplets in order to facilitate the guidance of the aerosol through the aeraulic circuit of the device and the respiratory pathways.

The atomizer includes a perforation mechanism produced by a cannula or hollow needle made, for example, of plastic or of metal placed at the center of the atomizer. This mechanism can include air bubble avoidance and liquid level measurement functions. This perforation device makes it possible to receive a sterile and watertight reservoir or vial that has a membrane seal made of elastomer material that can be perforated.

The atomizer is provided with a metal foil (or flexible circuit) serving as an electrode and making it possible to supply the ceramic with electricity which can be used to produce a depressurization sensor associated with the piezoelectric ceramic. The voltage generated on the ceramic during inhalation can be exploited to produce a device for triggering atomization on inhalation.

It follows that the invention is not limited to the embodiments described hereinabove. The latter are only examples.

It will also be noted that, in addition to the introduction of a longitudinal vibration mode, it is possible to provide a radial vibration mode.

DETAILED DESCRIPTION OF THE INVENTION

The invention will be better understood in this section by means of a detailed description and nonlimiting examples illustrated by the figures.

BRIEF DESCRIPTION OF THE FIGURES

FIG. 1 is a cross-sectional representation of an exemplary atomizer according to the invention.

FIGS. 2, 3, 4, 5, 6, 7, 8, 9, 10 and 13 are cross-sectional representations of variants of this atomizer.

FIG. 12 represent modelings of the vibrational behavior of the atomizer according to the present invention.

FIG. 13 is a cross-sectional representation of an atomizer including a tubular vibrating membrane placed around the "horn", itself vibrating according to a longitudinal mode.

FIGS. 14 & 15 respectively show the perspective view and the cross sections of the cylindrical tabular or truncated cone atomizers.

FIG. 16 represents the perspective view and the cross section of a simple T-shaped medical inhaler incorporating an atomizer as described by the present invention.

FIGS. 17A and 17B illustrate two configurations of an inhaler in "pocket" format incorporating an atomizer as described by the present invention. FIG. 17A represents an inhaler driven by an external electronic module. FIG. 17B represents an inhaler with the electronics incorporated in the module.

FIG. 17C shows a cross section of this same inhaler making it possible to see the position of the atomizer in its module.

FIG. 18 represents the cross section of an atomizer comprising the various air bubble evacuation and liquid presence sensor functions.

LIST OF NUMERICAL REFERENCE USED IN THE FIGURES

1. Piezoelectric transducer body
1*a* Stress concentration zone
1*b* Deformation amplification zone
2. Single-piece piezoelectric ceramic
3. Micro-perforated membrane
4. Cavity containing the liquid
5. Rear mass
6. Prestressing screw
7. Electrode
8. Link member
9. Multilayer piezoelectric ceramic
10. Bell mouth
11. Electrical ground return
12. Transducer cover
13. Reservoir
14. Plug
15. Module
16. Tip
17. Openings or valves
18. Power supply cables
19. Electronic module
20. Electrical connector
21. Coaxial tube
22. Liquid presence sensor
23. Sensor return cable The atomizer illustrated in FIG. 1A comprises a piezoelectric transducer body 1 that is preferably vibrated in the 50 kHz to 200 kHz range. FIG. 1B illustrates the same atomizer, but with a curve illustrated alongside it showing the maximum amplitude of the longitudinal displacements of the various parts of the atomizer. The piezoelectric transducer body 1 is characterized by two zones: a stress concentration zone 1*a* and a deformation amplification zone 1*b*. In FIGS. 1 to 6, the external diameter of the stress concentration zone 1*a* is identical to the external diameter of the deformation amplification zone 1*b*. However, the internal diameter of the deformation amplification zone 1*b* is greater than the internal diameter of the stress concentration zone 1*a*.

In the atomizers illustrated in FIGS. 7 to 9, the external diameter of the stress concentration zone 1*a* is greater than the external diameter of the deformation amplification zone 1*b*. However, the internal diameter of the deformation amplification zone 1*b* is identical to the internal diameter of the stress concentration zone 1*a*.

FIG. 8B represents the same type of information as FIG. 1B, namely a curve showing the maximum amplitude of the longitudinal displacements of the various parts of the atomizer. The interior of the deformation amplification zone 1*b* comprises a cavity 4 containing the liquid to be atomized. In some cases, see in particular FIGS. 5, 7 and 8 to 10, the cavity 4 extends inside the stress concentration zone 1*a*. With this configuration, the ultrasound energy is retained primarily in the deformation amplification zone 1*b*, which constitutes a vibratory displacement amplifier. The conservation of energy in the deformation amplification zone 1*b* requires a conversion of the deformation stresses.

One or more piezoelectric members, preferably comprising a single-piece 2 or multilayer 9 piezoelectric ceramic, are located in the top part of the atomizer, at the level of the stress concentration zone 1*a*. FIG. 1, for example, represents two single-piece piezoelectric ceramics 2 connected by a central electrode 7, for example made of brass.

The rear mass 5 (dynamic mass) makes it possible to reduce the deformations at the rear of the piezoelectric ceramics. The prestressing screw 6 makes it possible to mechanically link all of this stack. This assembly constitutes a piezoelectric transducer which is an electromechanical converter which vibrates according to a longitudinal mode. A longitudinal mode is defined by the fact that the transducer is deformed along its symmetry axis by elongation or contraction of its section. The vibratory behavior of this type of transducer is governed essentially by its length so that the ratio of the overall length of the transducer to the diameter or width of the piezoelectric ceramic is, preferably, greater than or equal to 1.

The micro-perforated membrane 3 or a grid of small thickness (20 to 200 μm) is mechanically fixed to the end of the piezoelectric transducer body 1 where its vibratory speed is maximum. The fixing of the membrane 3 is such that the latter is acoustically coupled to the transducer in the zone 1*b*. In a first deformation mode and by way of example, this transducer is deformed and vibrates according to its half-wavelength. FIG. 1B shows the trend of the displacement of the points of the transducer in a section along its symmetry axis (length).

FIG. 2 shows this same atomizer provided with a membrane linked mechanically and acoustically to the transducer via a link member 8 making it possible to provide a high prestress to the membrane. Generally, the membrane can be mechanically coupled to the amplification zone by gluing, by brazing, by crimping or by welding. In particular, laser welding can be used.

FIG. 3 is a variant of the transducer where the rear mass is eliminated for reasons of construction simplicity. The transducer is dimensioned so that the displacement at the level of the single-piece piezoelectric ceramic 2 is as small as possible and as great as possible in the amplification zone 1*b*. The electrode 7 can be made up by fixing a brass foil for example or by gluing a flexible printed circuit on polyimide.

FIG. 4 represents a variant of the invention using a multilayer piezoelectric ceramic 9. The layers have a thickness, for example, of 20 to 200 μm and the use of such multilayers makes it possible, at lower cost, to reduce the electrical power supply voltage at the terminals of the ceramic. This configuration is of great benefit for applications that demand a cell or battery power supply.

Figure 3:
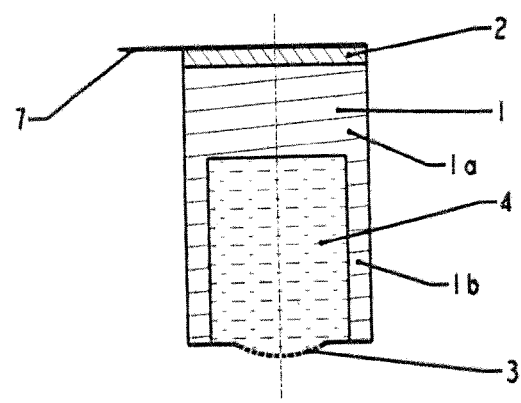
Figure 4:
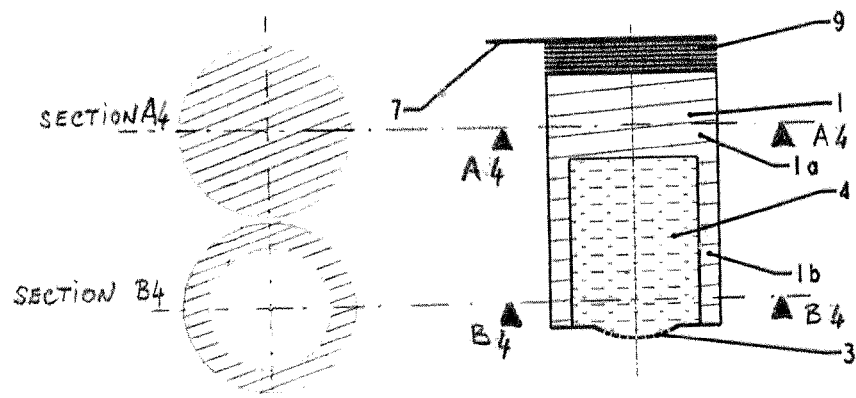
Figure 5:
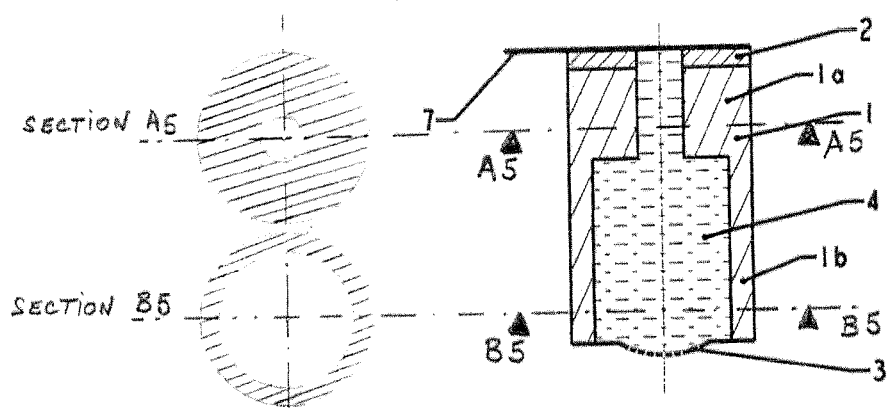

FIG. 5 shows a variant of the invention where the cavity (chamber) containing the liquid 4 crosses the body of the transducer 1 through its entire length. In this case, the single-piece piezoelectric ceramic 2 has a hole in its center. This configuration makes it possible to easily feed the cavity with liquid.

FIG. 6 shows another type of liquid feed by forming passages, holes or grooves to have the cavity filled with liquid 4 communicate with the outside. This configuration makes it possible to place the liquid reservoir around the transducer.

In the embodiment of FIGS. 7 and 8, the cavity containing the liquid 4 is tabular for reasons of simplicity of shape.

In the configuration of FIG. 7, the ceramic 2 is no longer situated at the rear of the body of the transducer 1 but at the level of the displacement amplifier in front of the stress concentration zone 1a. The single-piece piezoelectric ceramic 2 is thus protected by the body of the transducer 1.

This configuration offers the advantage of not having the ceramic 2 in contact with the liquid and of not posing problems of seal-tightness with the reservoir. The section variation of the body of the transducer 1 still makes it possible to amplify the vibratory displacement at the level of the membrane 3.

Figure 9:
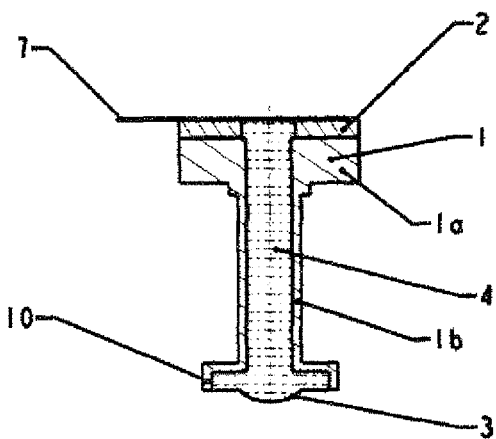

FIG. 9 shows another embodiment where the transducer 1 comprises a bell mouth 10 to which is mechanically and acoustically fixed a micro-perforated membrane 3. The advantage of this configuration is that it increases the atomized liquid throughput by simple surface effect while maintaining a high level of vibratory displacement amplification.

Figure 10:
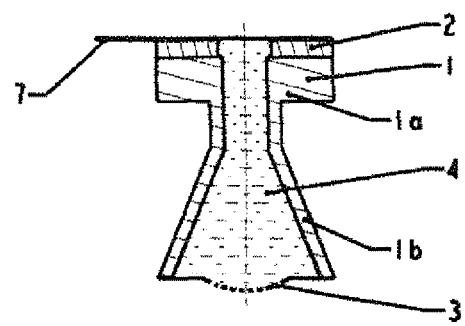

FIG. 10 illustrates, by way of example, a geometry in truncated cone shape of the vibratory displacement amplifier 1b. This configuration makes it possible to increase the dimension of the micro-perforated membrane 3.

Figure 11:
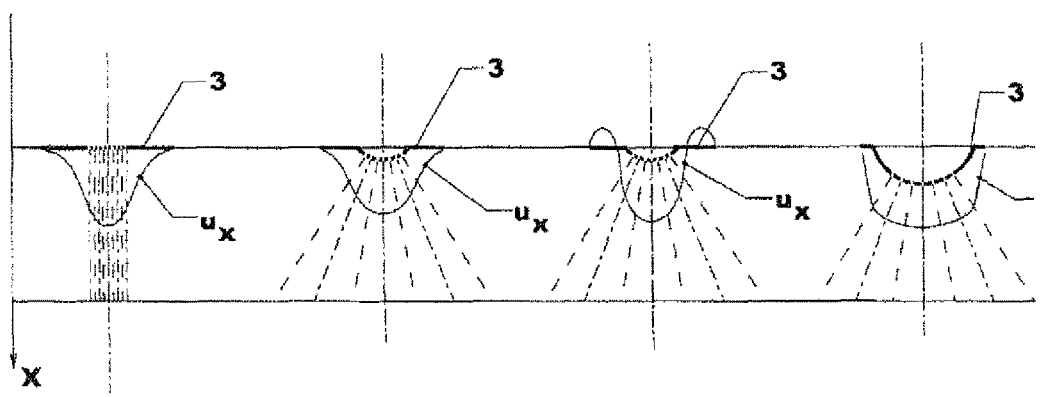
FIG. 11 represent the deformations of the membranes according to the structure of the atomizers.

FIG. 11 explains the vibratory operation of the micro-perforated membrane 3. In the structures resulting from the prior art (11A, 11B, 11C), the atomizer operates in flexing mode by coupling an annular piezoelectric ceramic with the micro-perforated membrane. When the membrane is flat (FIG. 11A), the maximum vibratory displacement ($U_x$) is situated in the center of the membrane and decreases strongly as the distance from the center increases. In this case, the jet is highly directional. When the membrane is dished and comprises a dome (FIGS. 11B and 11C), the latter increases the rigidity of the vibration mode and causes the jet to diverge by simple geometrical effect. This is observed regardless of the flexing vibration mode concerned. The flexing mode 1 is more advantageous from this point of view. In the case of the present invention (11D), the geometry and the nature of the membrane do not influence the vibration mode of the atomizer. In practice, the flexing stiffness of the membrane has no influence on the longitudinal deformation of the transducer. To obtain the best result, it is enough for the diameter of the dome to be very close to that of the transducer in order for the membrane to simply follow the maximum vibratory displacement at this point. Such a configuration provides the atomizer with greater efficiency and therefore decreases consumption for an identical atomization throughput. Furthermore, the jet is particularly uniform and diffuse.

FIGS. 12A and 12B show the deformations simulated by finite element calculations of an atomizer produced according to the present invention and given as an example.

In this specific case, the body of the transducer 1 is made of stainless steel. The internal cavity containing the liquid 4 has a diameter of 6 mm and the stress concentration zone 1a has an external diameter of 16 mm.

The deformation amplification zone 1b has an external diameter of 8 mm. The single-piece piezoelectric ceramic 2 is a PIC 255 (Physic Instruments) ceramic with an internal diameter of 8 mm, an external diameter of 16 mm and a thickness of 1 mm.

The lengths of the transducer 1 and of the deformation amplification zone 1b are respectively 16 mm and 12 mm. The microperforated membrane 3 has been made of electroformed nickel provided with 800 holes with a diameter of 5 μm. The thickness of the membrane is 50 μm and it has an external diameter of 8 mm. The dome has a height of 0.8 mm for a diameter of 5 mm. The membrane is fixed to the transducer by gluing. The longitudinal modes concerned have respectively resonance frequencies of 77 kHz and 120 kHz.

In the embodiment according to FIG. 13, the microperforated membrane 3 has a cylindrical or tubular geometry. The membrane is fixed on the one hand to the stress concentration zone 1a and on the other hand to the deformation amplification zone 1b. In this case, the membrane vibrates according to a radial mode.

FIGS. 14 and 15 show exemplary embodiments that have given excellent results in terms of droplet size and aerosol throughput. FIGS. 14A and 14B describe in perspective and in cross section a transducer 1 whose body has been made of stainless steel. The internal cavity containing the liquid 4 has a diameter of 6 mm and the stress concentration zone 1a has a diameter of 16 mm. The reservoir fixing mechanism, in this specific configuration, takes the form of a rear mass 5 in which threading has been formed. The external diameter and the length of this rear mass are respectively 10 mm and 8 mm. The single-piece piezoelectric ceramic 2 is a PIC 255 (Physic Instruments) ceramic with an internal diameter of 8 mm, an external diameter of 16 mm and a thickness of 1 mm. The deformation amplification zone 1b (or "horn") has an external diameter of 7 mm and a length of 12 mm.

The electrode 7 for electrically connecting the single-piece piezoelectric ceramic 2 is foil of stainless steel measuring 30 mm in diameter and 50 μm in thickness. The electroformed nickel membrane 3 comprises 10 800 2 μm holes for a thickness of 20 μm. The atomizer has made it possible to obtain droplets with a size of 2 μm for a throughput of 0.6 ml/min for an operating frequency of 80 kHz. FIGS. 15A and 15B describe in perspective and in cross section an atomizer whose transducer body 1 has been made of stainless steel. The internal cavity containing the liquid 4 has a diameter that varies from 6 mm to 12 mm and the stress concentration zone 1a has a diameter of 20 mm. The reservoir fixing mechanism, in this specific configuration, takes the form of a rear mass 5 in which threading has been formed. The external diameter and the length of this rear mass are respectively 10 mm and 8 mm. The single-piece piezoelectric ceramic 2 is a PIC 255 (Physic Instruments) ceramic with an internal diameter of 10 mm an external diameter of 20 mm and a thickness of 1 mm. The deformation amplification zone 1b (or "horn") of conical shape has an external diameter that varies firm 7 mm to 14 mm and a length of 9 mm.

The electrode 7 for electrically connecting the single-piece piezoelectric ceramic 2 is made of stainless steel 30 mm in diameter and 50 µm thick. The electroformed nickel membrane 3 comprises 45 300 2 µm holes for a thickness of 20 µm. The atomizer has made it possible to obtain droplets with a size of 2 µm for a throughput of 2.5 ml/min for an operating frequency of 70 kHz.

FIGS. 16A and 16B describe an inhaler for delivering medicines by pulmonary pathway. This inhaler can take the form of a mouthpiece 16 associated with a T-shaped module 15 supplied, for example, by Intersurgical, in which is incorporated the atomizer that is the subject of the present invention. The atomizer is placed in the module 15 using a transducer cover 12. The reservoir 13 provided with its plug 14 bears the transducer 1. The single-piece piezoelectric ceramic 2 is supplied with power by the electrode 7 in the form of a foil. The atomizer is supplied via cables 18. When the atomizer is operating, the latter generates an aerosol inside the module 15. The patient inhales the aerosol generated in this way, via the mouthpiece 16.

FIG. 17 describe another form of inhaler. FIG. 17A represents an inhaler incorporating the atomizer that is the subject of the present invention in which the electronic module 19 is placed outside and is linked to the module 15 of the inhaler by a cable 18. This inhaler includes a mouthpiece 16, a reservoir 13 lined to the atomizer and a plug 14. Openings 17 have been formed in the module 15 to manage the airflows and the aerosol produced by the atomizer.

FIG. 17B represents an inhaler in which the electronic module 19 is incorporated in the module 15 of the "pocket" inhaler.

FIG. 17C represents, in cross section, the inhaler of FIG. 17A. It shows the module 15 made, for example, of molded plastic, the tip 16 which can be removable and disposable after use, the transducer cover 12 which makes it possible to mount the atomizer in the module 15 and connect it to the electronic module 19 via the connector 20 and cable 18. The atomizer comprises the body of the transducer 1, the single-piece piezoelectric ceramic 2, the vibrating membrane 3, the electrode 7, the ground return 11, the reservoir 13 and the plug 14. The aerosol is generated in the cavity of the module 15 and sucked in by the patient through the mouthpiece 16.

FIG. 18 is a cross section of an atomizer provided with a tube making it possible to evacuate air bubbles and a liquid presence sensor. This atomizer comprises a tubular transducer body 1, a single-piece piezoelectric ceramic 2, a micro-perforated vibrating membrane 3 and a rear mass 5 making it possible to fix the reservoir 13. The single-piece piezoelectric ceramic 2 is supplied with power by a cable 18 connected on the one hand to the ground return 11 and to the electrode 7. A tube 21, preferably made of plastic and for example with a diameter of 3 mm, is placed inside the liquid cavity 4 in a coaxial manner. When the liquid throughput of the atomizer becomes high, the membrane 3 creates a depression such that air can penetrate inside the cavity containing the liquid 4. The formation of air bubbles at the level of the membrane 3 can block the formation of the aerosol and adversely affect the operation of the atomizer. The tube 21 makes it possible to evacuate the air bubbles by the action of the capillary forces that it exerts on the air-liquid interface. This same tube 21 has at its center an electrically conducting wire 23, the end 22 of which is in direct or indirect electrical contact with the liquid. A low-frequency alternating electrical signal, preferably at 500 Hz, is transmitted to the conducting wire 23. Since the membrane 3 and the transducer body 1 are not at the same electrical potential, the result is a current due to the resistivity of the liquid present in the cavity 4. The existence of this current corresponds to the presence of the liquid. The information originating from the liquid presence sensor 22 makes it possible to start or stop the operation of the atomizer automatically.

The invention is obviously not limited to the examples discussed hereinabove. Similarly, it is not limited to the medical field. The atomizer according to the invention can also be used as a diffuser of odors and perfume and/or in the application of cosmetic products. The invention also covers the diffusion of various liquid mists for local use (humidifiers or lubricators) or liquid handling devices for biotechnologies or reagents.

The invention claimed is:

1. A micro-perforated vibrating membrane piezoelectric atomizer comprising:

a rigid piezoelectric transducer body having a first end defining an opening and a second end, an inside of the piezoelectric transducer body comprising a cavity for containing a liquid to be atomized, and said body further comprising a symmetry axis, a micro-perforated vibrating membrane covering said opening, wherein the micro-perforated vibrating membrane has an internal side toward the cavity and an external side away from the cavity and has micro-holes having a shape with equivalent diameter ranging from 1 μm to 100 μm, wherein the liquid does not seep from the membrane when the atomizer is not activated, and wherein the liquid does pass through the membrane when the atomizer is activated such that there is a vibratory speed causing displacement of the membrane, and wherein the rigid piezoelectric transducer body comprises a constant cylindrical section from the opening to a singular annual flange, with an annular piezoelectric member located just downstream of the flange element, wherein the piezoelectric member is adapted and arranged so as to vibrate the piezoelectric transducer body, wherein the piezoelectric member is positioned closer to the second end than the first end in order to vibrate the piezoelectric transducer body in a direction parallel to the body's symmetry axis, wherein said vibrating membrane is directly connected to the first end, wherein said vibrating membrane is mechanically coupled to the first end by gluing, brazing, crimping, welding, or overmoulding, and wherein said vibrating membrane is acoustically coupled to the first end.

2. The atomizer as claimed in claim 1, wherein a section of the piezoelectric transducer body varies over its length.

3. The atomizer as claimed in claim 2, wherein the section varies discontinuously.

4. The atomizer as claimed in claim 3, wherein the section varies abruptly at a single point.

5. The atomizer as claimed in claim 4, wherein the thickness of the walls of the piezoelectric transducer body toward said second end is greater than the thickness of the walls of the piezoelectric transducer body toward the first end.

6. The atomizer as claimed in claim 5, wherein the piezoelectric transducer body is hollow toward said second end.

7. The atomizer as claimed in claim 2, wherein the internal diameter of the piezoelectric transducer body is constant.

8. The atomizer as claimed in claim 1, wherein the piezoelectric member is located against the external face of said second end.

9. The atomizer as claimed in claim 8, comprising a rear mass located against the external face of the piezoelectric member.

10. The atomizer as claimed in claim 1, wherein the external diameter of the piezoelectric transducer body is variable.

11. The atomizer as claimed in claim 10, wherein the external diameter toward said second end is greater than the external diameter toward said first end.

12. The atomizer as claimed in claim 11, of which the external face of the piezoelectric transducer body is defined by a first diameter and a second diameter, the transition zone between the two diameters forming an abrupt discontinuity.

13. The atomizer as claimed in claim 12, wherein the piezoelectric member is positioned in the discontinuity and bears on the portion of the piezoelectric transducer body that includes the second end.

14. The atomizer as claimed in claim 1, wherein the ratio between the length and the diameter of said cavity is greater than 0.5.

15. The atomizer as claimed in claim 1, wherein the micro-perforated membrane at least partially forms a dome which provides a vibratory motion amplification effect.

16. The atomizer as claimed in claim 1, wherein the micro-perforated membrane has a thickness between 20 and 200 µm and includes holes of a diameter between 1 µm and 100 µm.

17. The atomizer as claimed in claim 1, wherein the piezoelectric member is a multi-layer ceramic.

18. A micro-perforated vibrating membrane piezoelectric atomizer comprising:
    a rigid piezoelectric transducer body having a first end defining an opening and a second end, an inside of the piezoelectric transducer body comprising a cavity for containing a liquid to be atomized, and said body further comprising a symmetry axis,
    a micro-perforated vibrating membrane covering said opening, and wherein the micro-perforated vibrating membrane has an internal side toward the cavity and an external side away from the cavity and has micro-holes having a shape with equivalent diameter ranging from 1 µm to 100 µm, wherein the liquid does not seep from the membrane when the atomizer is not activated, and wherein the liquid does pass through the membrane when the atomizer is activated such that there is a vibratory speed causing displacement of the membrane, and
    wherein the rigid piezoelectric transducer body comprises a constant diameter cylindrical section from the opening to a singular annular flange, with an annual piezoelectric member located just downstream of the flange,
    wherein the piezoelectric member is positioned closer to the second end than the first end in order to vibrate the piezoelectric transducer body in a direction parallel to the body's symmetry axis,
    wherein said vibrating membrane is mechanically fixed to the first end, whereby the mechanical fixing is achieved via use of a non-moveable direct connection of the vibrating membrane to the first end, and
    wherein said vibrating membrane is acoustically coupled to the first end.

19. The atomizer as claimed in claim 18, wherein a section of the piezoelectric transducer body varies over its length.

20. The atomizer as claimed in claim 19, wherein the section varies discontinuously.

21. The atomizer as claimed in claim 20, wherein the section varies abruptly at a single point.

22. The atomizer as claimed in claim 21, wherein the thickness of the walls of the piezoelectric transducer body toward said second end is greater than the thickness of the walls of the piezoelectric transducer body toward the first end.

23. The atomizer as claimed in claim 22, wherein the piezoelectric transducer body is hollow toward said second end.

24. The atomizer as claimed in claim 19, wherein the internal diameter of the piezoelectric transducer body is constant.

25. The atomizer as claimed in claim 18, wherein the piezoelectric member is located against the external face of said second end.

26. The atomizer as claimed in claim 25, comprising a rear mass located against the external face of the piezoelectric member.

27. The atomizer as claimed in claim 18, wherein the external diameter of the piezoelectric transducer body is variable.

28. The atomizer as claimed in claim 27, wherein the external diameter toward said second end is greater than the external diameter toward said first end.

29. The atomizer as claimed in claim 28, of which the external face of the piezoelectric transducer body is defined by a first diameter and a second diameter, the transition zone between the two diameters forming an abrupt discontinuity.

30. The atomizer as claimed in claim 29, wherein the piezoelectric member is positioned in the discontinuity and bears on the portion of the piezoelectric transducer body that includes the second end.

31. The atomizer as claimed in claim 18, wherein the ratio between the length and the diameter of said cavity is greater than 0.5.

32. The atomizer as claimed in claim 18, wherein the micro-perforated membrane at least partially forms a dome which provides a vibratory motion amplification effect.

33. The atomizer as claimed in claim 18, wherein the micro-perforated membrane has a thickness between 20 and 200 µm and includes holes of a diameter between 1 µm and 100 µm.

34. The atomizer as claimed in claim 18, wherein the piezoelectric member is a multi-layer ceramic.

35. The micro-perforated vibrating membrane piezoelectric atomizer as claimed in claim 1, wherein the atomizer has a deformation amplification zone with a substantially constant outer diameter.

36. The atomizer as claimed in claim 18, wherein the atomizer has a deformation amplification zone with a substantially constant outer diameter.

* * * * *